(12) United States Patent
Northcutt et al.

(10) Patent No.: US 10,779,954 B1
(45) Date of Patent: Sep. 22, 2020

(54) BODY DENSITY SCAN RESULT-MATCHED ORTHOPEDIC IMPLANTS AND METHODS OF USE

(71) Applicant: Aurora Spine, Inc., Carlsbad, CA (US)

(72) Inventors: Trent James Northcutt, Oceanside, CA (US); Laszlo Garamszegi, Mission Viejo, CA (US)

(73) Assignee: AURORA SPINE, INC., Carlsbad, CA (US)

( * ) Notice: Subject to any disclaimer, the term of this patent is extended or adjusted under 35 U.S.C. 154(b) by 0 days.

(21) Appl. No.: 15/840,697

(22) Filed: Dec. 13, 2017

Related U.S. Application Data

(60) Provisional application No. 62/433,345, filed on Dec. 13, 2016.

(51) Int. Cl.
| | |
|---|---|
| *A61F 2/46* | (2006.01) |
| *A61F 2/44* | (2006.01) |
| *A61F 2/34* | (2006.01) |
| *A61F 2/36* | (2006.01) |
| *A61B 6/00* | (2006.01) |
| *A61F 2/30* | (2006.01) |

(52) U.S. Cl.
CPC .............. *A61F 2/4455* (2013.01); *A61F 2/34* (2013.01); *A61F 2/3662* (2013.01); *A61B 6/505* (2013.01); *A61F 2002/3071* (2013.01); *A61F 2002/30593* (2013.01); *A61F 2002/30985* (2013.01)

(58) Field of Classification Search
CPC ........ A61F 2/4455; A61F 2/34; A61F 2/3662; A61F 2/46; A61F 2/4607; A61F 2/4609; A61F 2/4611; A61F 2/28; A61F 2/30; A61F 2/32; A61F 2/36; A61F 2/44; A61F 2002/30593; A61F 2002/3071; A61F 2002/30985; A61F 2002/30713; A61F 2002/30714; A61B 6/505
USPC ............................................. 623/17.11–17.16
See application file for complete search history.

(56) References Cited

U.S. PATENT DOCUMENTS

| | | | | |
|---|---|---|---|---|
| 7,850,715 | B2 * | 12/2010 | Banouskou | ........ A61B 17/7037 606/246 |
| 9,301,845 | B2 * | 4/2016 | Bonutti | ..................... A61F 2/38 |
| 9,603,637 | B2 * | 3/2017 | Northcutt | ........... A61B 17/7068 |

* cited by examiner

*Primary Examiner* — Pedro Philogene
(74) *Attorney, Agent, or Firm* — Hybrid Law Group PC

(57) ABSTRACT

A method of treating a patient who requires surgical implantation of an orthopedic implant is described. The method includes the steps of: determining the DEXA scan T-score of the patient's native bone at a site of surgical implantation where the implant will be in contact with the patient's native bone; retrieve from among three or more implants of the same type an implant that has a density that is closest to the density of the patient's native bone at the site of surgical implantation based on the DEXA scan T-score of the patient's native bone; and implanting the retrieved implant in the patient to the exclusion of the other two or more implants.

23 Claims, 6 Drawing Sheets

BODY DENSITY SCAN RESULT-MATCHED ORTHOPEDIC IMPLANTS AND METHODS OF USE

RELATED APPLICATIONS

This application claims priority from U.S. Provisional Patent Application Ser. No. 62/433,345 filed Dec. 13, 2016, which is incorporated herein by reference in its entirety.

BACKGROUND

This invention relates generally to the field of orthopedic surgery involving orthopedic implants to correct or repair damaged bones, cartilage, vertebral discs and other musculoskeletal structures. Such surgery may include implants such as interbody fusion cage implants for spinal surgery to replace damaged or diseased vertebral discs, interspinous fixation implants, full or partial knee replacement implants, full or partial hip replacement implants and the like.

In patients scheduled to undergo orthopedic surgery, bone quality in the area of surgical intervention and implantation affects the safety and longevity of the prosthetic implant. For example, in patients undergoing joint arthroplasty of the hip, the bone quality around the joint affects the safety and failure rate and useful life span of the implant. BMD can also affect strategies employed in spinal fusion in osteoporotic spines.

Bone mineral density ("BMD") is a clinical marker for bone strength. Bone mineral density varies among different body regions and also varies as a result of age, disease, injury, general health, weight, demographic, and use of certain medications or hormones.

Although BMD at the site of intervention is correlated with long-term results, bone density scans of the diseased or damaged site are not always performed and even when they are performed, they do not affect the course of treatment in terms of the specific implant that is used. Thus, there is a one size fits all standard of care when it comes to orthopedic implants as they relate to the bone density of the area surrounding the implant.

Bone density scans are typically done using a dual energy x-ray absorptiometry ("DEXA") scan. A DEXA scan is a means of measuring bone density by directing two x-ray beams with different energy levels at the patient's bone at the diseased or injured site or the site of diagnosis for age-related routine scans to determine BMD. When soft tissue absorption is subtracted out, the BMD can be determined from the absorption of each beam by the bone. DEXA scans are the most widely used and most thoroughly studied bone density measurement technology for determining the density of bone.

Bone density scans prior to an orthopedic implant are not always the standard of care. For example, in one study, orthopedic surgeons were asked if BMD is important to them in performing hip arthroplasty (Maier G S, Kolbow K, Djorde L, Maus U. The Importance of Bone Mineral Density in Hip Arthroplasty: Results of a Survey Asking Orthopaedic Surgeons about Their Opinions and Attitudes Concerning Osteoporosis and Hip Arthroplasty. Adv. In Orthopedics. 2016, Article ID 8079354). 72% of all asked orthopaedics reported to use cementless implants as a standard in hip arthroplasty, and over 60% reported that low BMD is a reason to reconsider operation strategies, such as using cement if the patient has low BMD. However, only 4% performed BMD measurement preoperatively.

Another example where BMD is an important factor, albeit one that is not typically considered, in patient treatment is spinal fusion implants, including those that employ PEEk or titanium cages. Especially in older patients with osteoporosis, low BMD at the site of fusion is associated with poor fusion rate and bone stability. Various interventions have been proposed to address this problem, but most interventions focus simply on poor screw fixation or screw loosening and fixation failure. Many techniques have been employed to enhance the pullout strength of the pedicle screws that fix cages to the vertebrae. The preparation for screw hole or minimization of tapping hole can affect the pullout strength in osteoporotic bone and, although the anatomical constraints vary with patients, bigger and longer screws have been used to improve fixation to fragile bones. Other solutions involve the angulation of the screws and screw positioning in areas of higher BMD, either of which may increase pullout strength. These techniques may enhance fixation, but they still don't address the core problem of implant failure that results from poor bone BMD around the implant.

In fact, the current standard of care considers BMD around the site of intervention mainly as a factor to determine whether or not to perform a procedure, and sometimes, as discussed above, BMD is used as a factor to alter fixation methods, such as the screws. Otherwise, BMD is mostly used as a means of diagnosing the progression of osteoporosis in older patients, and is not a factor in the use and type of orthopedic implants.

Clinically, stiffening of the functional spinal unit (FSU) is a consequence of surgical intervention for fusion. While such a condition is unavoidable, Applicants believe that more focus is needed on developing a mechanical configuration that will provide sufficient stability yet not result in stress shielding due to an overly stiff construct. For example, as it relates to titanium cage interbody spinal fusion implants, the modulus of elasticity for trabecular bone has been reported to be approximately 0.10 GPa, while titanium displays a modulus of 110 GPa, and reinforced PEEK has a modulus of approximately 18 GPa. In short, the implants and the surrounding bone don't match, and there has been no focus in the clinic or the scientific literature on this mismatch and whether it leads to a higher than necessary incidence of failure in implants over time.

For example, in the case of spinal fusion, Applicants believe that interbody cage stiffness can affect surgical outcomes, particularly in osteoporotic bone. Unwanted subsidence or collapse of the vertebral endplates is an unfortunate result that happens too frequently. The patient's bone density scan is able to reveal the level of osteoporosis in the subject patient but no bone scan density result-matched interbody cage with semi-customized interbody implant is available at the present time, nor has such a matched method of intervention been contemplated until the present invention. Certainly there has been no effort to match a patient's DEXA scan with an implant that closely approximates the DEXA scan so that the implant and the surrounding bone at the site of intervention are similar in density. Nor has such a method been considered as a means of improving long-term outcome for patients with orthopedic implants, such as interbody spinal fusion cage implants or hip implants, among others.

There is a need to improve results in orthopedic implants. There is a need to customize implants based on the health and strength of the bone at the site of intervention. There is a need to improve fusion and minimize failure at the site of fusion. There is a need to deliver implants that match the mechanics of the surrounding tissue so that the new and the old are adapted to one another and one is not prone to cause the failure of the other. These are needs that have not been addressed until now.

SUMMARY

One object of the invention is to provide a spine surgery fusion product that has variable stiffness designs in order to match patients' bone density and be as close as possible to the modulus of the patient's own bone modulus. The modulus of elasticity variation of one embodiment of the current invention can be achieved by making the design hollow to create a "soft-cage" that has lower, medium or higher material density, and the various optional densities can be used to best match the implant to the bone at the site of intervention.

In various embodiments, the implants described herein can be manufactured from implantable metal, plastic, reinforced plastic, titanium, titanium cobalt, stainless steel, cobalt-chromium alloys, titanium and cobalt mixed metal, ceramic, PEEK or carbon fiber. The interbody cages described herein can be manufactured employing well known traditional manufacturing methods or newer methods such as 3-D printing.

In one embodiment, a kit for orthopedic surgical procedures is provided. The kit has three or more orthopedic implants of the same type. The first implant has a first density, the second implant has a second density that is lower than the first density, and the third implant has a third density that is lower than the first and second densities. Other than the density of the implants, the three implants are the same in outer dimension and will otherwise fit within the same space of a surgical site of intervention. The kit also includes instructions for use during a surgical procedure on a patient. The instructions include the following steps: determine the DEXA scan T-score of the patient's native bone at a site of surgical intervention;
  i. if the DEXA scan T-score of the patient's native bone is −1 or higher, then retrieve the first implant and introduce it to the patient's native bone to the exclusion of the second and third implants;
  ii. if the DEXA scan T-score of the patient's native bone is between a −2.5 and −1.0, then retrieve the second implant and introduce it to the patient's native bone to the exclusion of the first and third implants; and
  iii. if the DEXA scan T-score of the patient's native bone is lower than −2.5, then retrieve the third implant and introduce it to the patient's native bone to the exclusion of the first and second implants.

In one embodiment, the implants are interbody cages for spine fusion. In other embodiments, the implants are femoral stems of a hip implant or acetabular components of a hip implant.

In another embodiment, a method of treating a patient who requires surgical implantation of an orthopedic implant is described. The method includes the steps of: determining the DEXA scan T-score of the patient's native bone at a site of surgical implantation where the implant will be in contact with the patient's native bone; retrieve from among three or more implants of the same type an implant that has a density that is closest to the density of the patient's native bone at the site of surgical implantation based on the DEXA scan T-score of the patient's native bone; and implanting the retrieved implant in the patient to the exclusion of the other two or more implants. In one embodiment, the implants are interbody cages for spine fusion. In other embodiments the implants are femoral stems of a hip implant or acetabular components of a hip implant.

Other objects and advantages of the present invention will become apparent from the following descriptions, taken in connection with the accompanying drawings, wherein, by way of illustration and example, various embodiments of the present invention are disclosed.

BRIEF DESCRIPTION OF THE DRAWINGS

The drawings constitute a part of this specification and include exemplary embodiments to the invention, which may be embodied in various forms. It is to be understood that in some instances various aspects of the invention may be shown exaggerated or enlarged to facilitate an understanding of the invention.

DETAILED DESCRIPTION

Exemplary embodiments of the invention are shown in the accompanying figures and described below.

A bone mineral density (BMD) test provides a snapshot of bone health by providing a value associated with bone density. The more dense the bone, the healthier and stronger it is. The test is typically performed to identify osteoporosis, determine risk for fractures (broken bones), and measure response to osteoporosis treatment. It is not presently used to determine the appropriate density of an orthopedic implant for a patient undergoing an orthopedic surgical procedure requiring an implant.

Figure 7:
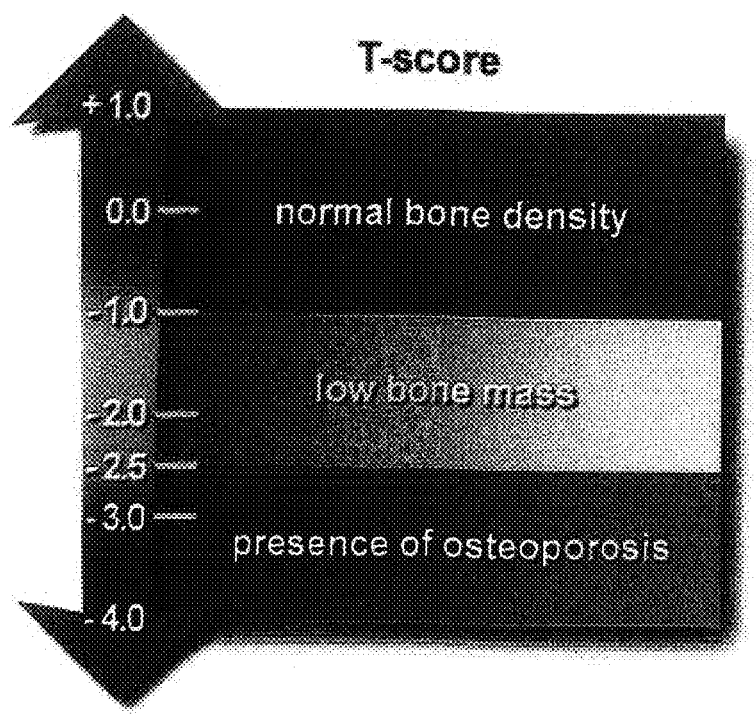
FIG. 7 is a DEXA Scan T score chart of the prior art.

The most widely recognized BMD test is called a central dual-energy x-ray absorptiometry, or central DEXA scan. The DEXA scan can measure bone density at the hip, spine and other bones. A DEXA scan measures BMD and compares it to that of an established norm or reference standard to give the patient a DEXA Scan score. The DEXA scan score is called a T-score, which is a value that compares the patient to an ideal or peak bone mineral density of a healthy 30-year old adult. A score of 0 means the BMD is equal to the norm for a healthy young adult. Differences between the patient's BMD and that of the healthy young adult norm are measured in units called standard deviations (SDs). The more standard deviations below 0, indicated as negative numbers, the lower the patient's BMD, meaning the less dense the bone. A DEXA scan T-score between +1 and −1 is considered normal or healthy. A DEXA Scan T-score between −1 and −2.5 indicates low BMD, although not low enough to be diagnosed with severe osteoporosis. A DEXA scan T-score of −2.5 or lower indicates osteoporosis and means that the BMD is very low. The greater the negative number, the more severe the osteoporosis and the less dense the bone. Thus, when the DEXA scan T-score is between +1 and −1 (or is higher than −1), the BMD of the bone is normal. When the DEXA scan score is between 1 and 2.5 SD below the young adult mean (−1 to −2.5 SD), then the BMD is lower than normal and indicates bone that is less dense than normal bone for that location. When the DEXA scan score is 2.5 SD or more below the young adult mean (−2.5 SD or lower) this indicates bone density that is significantly below normal for bone in that location and is an indicator of osteoporosis. These scores are typically associated with a DEXA scan chart, such as the one shown in FIG. 7, in which the normal range of +1 to −1 (or greater than −1) is represented in green, the below normal range of −1 to −2.5 is represented in yellow, and the very low range below −2.5 indicating osteoporosis is represented in red. This is a standard method of depicting the DEXA scan T-score in the medical community.

DEXA scan T-scores of the spinal column are typically matched to BMD as follows. BMD in $g/cm^2$ of about 1.10 and higher are associated with a normal bone density and are therefore given a DEXA scan T-score of at least −1 or higher (meaning 0, +1 and higher), i.e., in the green range. BMD in $g/cm^2$ of about 0.90 to about 1.10 are associated with low bone mass and are therefore given a DEXA scan T-score of between −1 and −2.5, i.e., in the yellow range. Finally, BMD in $g/cm^2$ below about 0.90 are associated with very low bone mass and osteoporosis and are therefore given a DEXA scan T-score of below 2.5, i.e., in the red range.

The present invention provides methods of treatment and orthopedic implant kits that allow physicians to best match the implant with their patient's DEXA Scan T-score such that the implant that most closely approximates the density of the bone at the site of implantation relative to other implants is the one that is implanted to the exclusion of the other implants of the same type. When given the choice of three or more implants of the same type that only differ by density, surface area, and porosity, the surgeon can choose the implant that most closely approximates the patient's native bone at the site of implantation based on the patient's DEXA Scan T-score.

Figure 1:
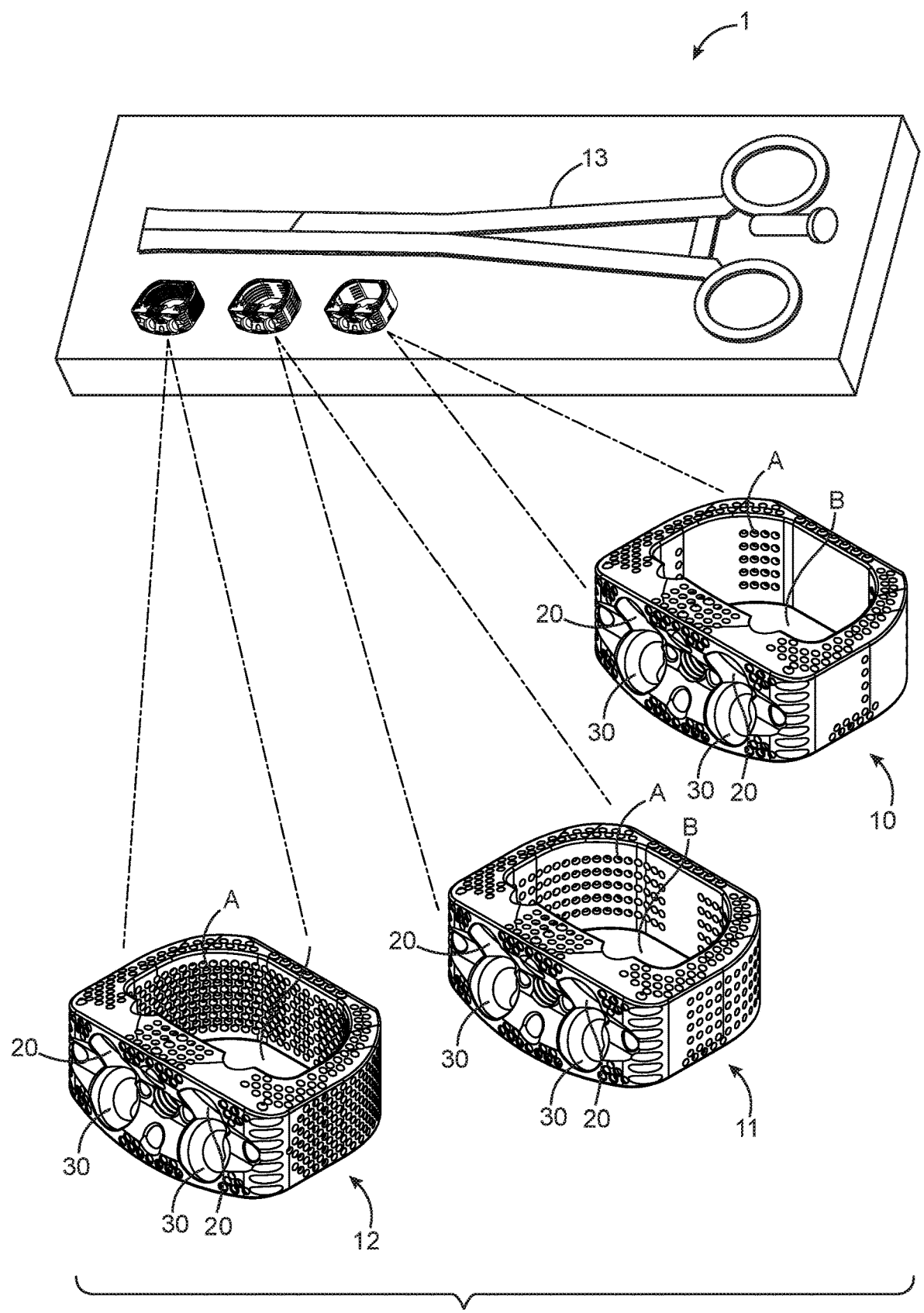
FIG. 1 is a perspective view of a kit of three interbody spinal fusion cage implants.

One embodiment of the invention is illustrated in FIG. 1. FIG. 1 shows three interbody spinal fusion cage implants that are part of a kit 1. Spinal fusion cage implants are well known in the art and they come in various sizes and shapes to fit within the lumbar, thoracic or cervical spine. One example of an interbody spinal fusion cage is the Discovery™ minimally invasive cervical interbody spinal fusion cage made by Aurora Spine. There are many other examples made by many other manufacturers from many different shapes, sizes and materials.

Kit 1 contains cage 10, cage 11, and cage 12. It also contains an inserter 13 for inserting cages 10, 11 or 12 into the disk space in between two vertebral bodies in the spinal column of a patient, as well as instructions for use (not shown). Kit 1 may also include one or more sizers to determine the correct size of interbody cage implant to insert into the disk space. Kit 1 may also include graft material that is packed into the hollow space B in the center of cages 10, 11 or 12. Each of cages 10, 11, and 12 have outer dimensions that are virtually identical, meaning they are the same or about the same height, width, and depth. However, they are not the same weight, and they do not have the same density, porosity or amount of surface area. Cage 10 is the heaviest of the three cages, has the least porosity, the least surface area and the most density. Cage 11 weighs less than cage 10 but more than cage 12. Cage 11 has more porosity, more surface area, and less density than cage 10 but less porosity, less surface area and more density than cage 12. Cage 12 weighs less than both cage 10 and cage 11. Cage 12 has more porosity, more surface area, and less density than both cages 10 and 11. Cages 10, 11 and 12 can be manufactured from implantable metal, plastic, reinforced plastic, titanium, titanium cobalt, stainless steel, cobalt-chromium alloys, titanium and cobalt mixed metal, ceramic, PEEK or carbon fiber, or combinations of any of the above. In one embodiment, they are manufactured from titanium. The weight, density, surface area, and porosity of the three cages differs as a result of the number and positioning of various hollow channels A through the cages, which run through the solid surfaces of the cages. The cage with the most number of hollow channels running through it has the most porosity, is the lightest in weight, is the lowest in density, and has the most surface area. Cage 12 is has the most porosity, least density, lowest weight and highest surface area among the three cages in kit 1, because it has the most number of hollow channels A running through its otherwise solid body. Cage 12 therefore has the least resistance to crush under load and is most similar to osteoporotic bone having a DEXA Scan T-score of −2.5 or lower (in the red range of a DEXA scan T-score) as compared to cages 11 and 10. Cage 11 has fewer hollow channels A running through it than cage 12 but has more hollow channels A than cage 10. Cage 11 is heavier, less poros, more dense, and has less surface area than cage 12, but is lighter in weight, more poros, less dense, and has more surface area than cage 10. Therefore, cage 11 is more dense than cage 12 but less dense than cage 10 and is most similar to low density bone at the T-Score range of −1 to −2.5 (in the yellow range of a DEXA scan T-score) as compared to the other two cages 10 and 12. Cage 10 has fewer hollow channels A than both cages 11 and 12, and is therefore the heaviest in weight, least poros, most dense, and have the least amount of surface area of cages 10, 11 and 12 of kit 1. Cage 10 has the strongest resistance to crushing under load compared to cages 11 and 12. Cage 10 is therefore the cage among cages 10, 11 and 12 that is most similar to healthy bone having a DEXA scan T-score range of −1 or higher (in the green range of a DEXA scan T-score) as compared to the other two cages 11 and 12.

Turning to cage 10, it has the highest density of the three cages. In one embodiment, it has a density of about 4.40 $g/cm^3$, but can range from about 3.90 $g/cm^3$ to about 5.00 $g/cm^3$ in density. In another embodiment, it has a density of about 3.90 $g/cm^3$. In another embodiment, it has a density of about 3 $g/cm^3$, but it can range from about 2 $g/cm^3$ to about 4 $g/cm^3$ in density. In another embodiment, it has a density of about 1.40 $g/cm^3$, but can range from about 1.10 $g/cm^3$ to about 1.80 $g/cm^3$ in density. In another embodiment, Turning to cage 11, it has a density that is in between the densities of cage 10 and cage 12, meaning it is less dense than cage 10 but more dense than cage 12. In one embodiment, it has a density of about 3.80 $g/cm^3$, but range from about 3.30 $g/cm^3$ to about 4.20 $g/cm^3$ in density. In one embodiment, it has a density of about 3.30 $g/cm^3$. In another embodiment, it has a density of about 2.00 $g/cm^3$, but can range from about 1.00 $g/cm^3$ to about 3.00 $g/cm^3$ in density. In another embodiment, it has a density of about 1 $g/cm^3$, but can range from about 0.90 $g/cm^3$ to about 1.10 $g/cm^3$ in density.

Turning to cage 12, it has a density that is lower than both cage 10 and cage 11 of the cages in kit 1. In one embodiment, it has a density of about 3.20 $g/cm^3$, but range from about 2.50 $g/cm^2$ to about 3.60 $g/cm^2$ in density. In one embodiment, it has a density of about 2.50 $g/cm^3$. In another embodiment, it has a density of about 1.50 $g/cm^3$, but can range from about 1.00 $g/cm^3$ to about 2.5 $g/cm^3$. In another embodiment, it has a density of about 0.80 g/cm³, but can range from about 0.60 g/cm³ to about 0.90 g/cm³ in density.

In another embodiment, not shown in the figures, kit 1 may contain a fourth cage that is still lower in density than cage 12, and is used to match DEXA scan T-scores that are lower than −3 suggesting not only osteoporosis but potentially a fracture. In one embodiment, the fourth cage has a density of about 2.50 g/cm³, but can range from about 2.00 g/cm³ to about 3.00 g/cm³ in density. In another embodiment, it has a density of about 1.00 g/cm³ but can range from about 0.40 g/cm³ to about 1.3 g/cm³ in density. In another embodiment, it has a density of about 0.60 g/cm', but can range from about 0.40 g/cm³ and about 0.70 g/cm³ in density.

In one embodiment, cages 10, 11 and 12 have identifying indicia that indicate whether they are the most dense (also heaviest, least porous and least surface area), middle density (middle heavy, middle porous and middle surface area), or least dense (least heavy, most porous and most surface area) of the 3 cages. For example, the cages can be numbered 1 for cage 10, 2 for cage 11 and 3 for cage 12 or the reverse etched into the cages. In another embodiment, their relative density/porosity/weight/surface area may be identified by a +− and = signs etched into the cages. In another embodiment, the cages may have a color painted on an area of the cage or the entirety of the cage. For example, cage 10 may be green, cage 11 may be yellow and cage 12 may be red to match the typical DEXA Scan color coded results. In another embodiment, each of cages 10, 11 and 12 is located within a sealed package of its own that itself has an identifier that indicates whether it is the most dense/least porous/heaviest/lowest surface area, middle density/porosity/weight/surface area or least dense/most porous/lightest/highest surface area of the cages. For example, cage 10 may be in a sealed package that is green or has green markings on it; cage 11 may be in a sealed package that is yellow or has yellow markings on it; and cage 12 may be in a sealed package that is red or has red markings on it. The purpose of this is so that the team of surgeons and staff that are involved in a surgical procedure can easily identify which of the cages 10, 11, or 12 they should use based on the DEXA scan T-score of the patient's spinal column at the site of intervention, and they won't make a mistake by implanting the wrong cage.

Figure 2:
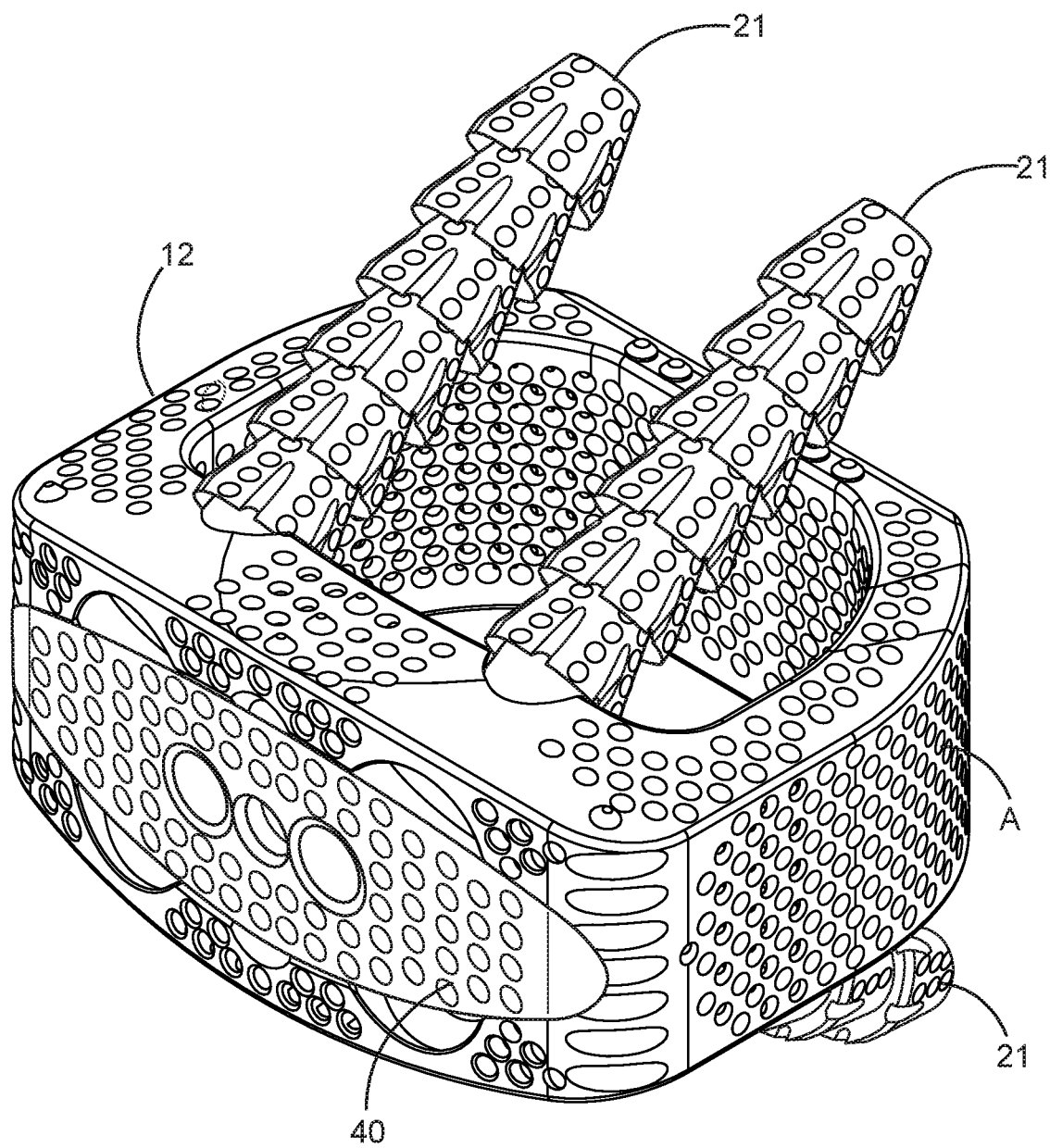
FIG. 2 is a perspective view of one of the interbody spinal fusion cage implants from the kit of FIG. 1 with anchors and an anchor plate.

FIG. 2 shows an exemplary embodiment of a cage 12 with anchors 21 and anchor plate 40. The anchors 31 and anchor plate 40 also fit and are used with cages 10 and 11 in the same manner. Each of cages 10, 11 and 12 also has a center hole B where bone graft material can be packed prior to insertion into disk space within a spinal column of a patient. Anchors 21 have the same density as the cages with which they are associated. Anchors 21 can be made with the right amount of holes or channels A to give the anchors the density level that matches the density of the cage with which they are matched and packaged. Thus, anchors 21 can have the same density as cage 10, the same density as cage 11, or the same density as cage 12. Anchors 21 that are matched with cage 10 in density have the least amount of holes or channels compared to anchors 21 that are matched with cages 11 or 12. Anchors 21 that are matched with cage 11 in density have fewer holes or channels A than anchors 21 that are matched with cage 12 but more holes or channels A than anchors 21 that are matched with cage 10. Anchors 21 that are matched with cage 12 in density have the most amount of holes or channels compared to anchors 21 that are matched with cages 11 or 12. Anchors 21 can have the same indicia identifying their density level as cages 10, 11 and 12, therefore indicating which of cages 10, 11 or 12 they match.

In one embodiment, anchors 21 that are matched in density with cage 10 are located in a sealed package with cage 10. As described above, the sealed package can be green in color or have green markings. And anchors 21 that are matched in density with cage 11 are located in a sealed package with cage 11. As described above, the sealed package can be yellow in color or have yellow markings. And anchors 21 that are matched in density with cage 12 are located in a sealed package with cage 12. As described above, the sealed package can be red in color or have red markings. This way it becomes more difficult to incorrectly match anchors 21 with the wrong counterpart cages 10, 11, or 12.

Figure 3:
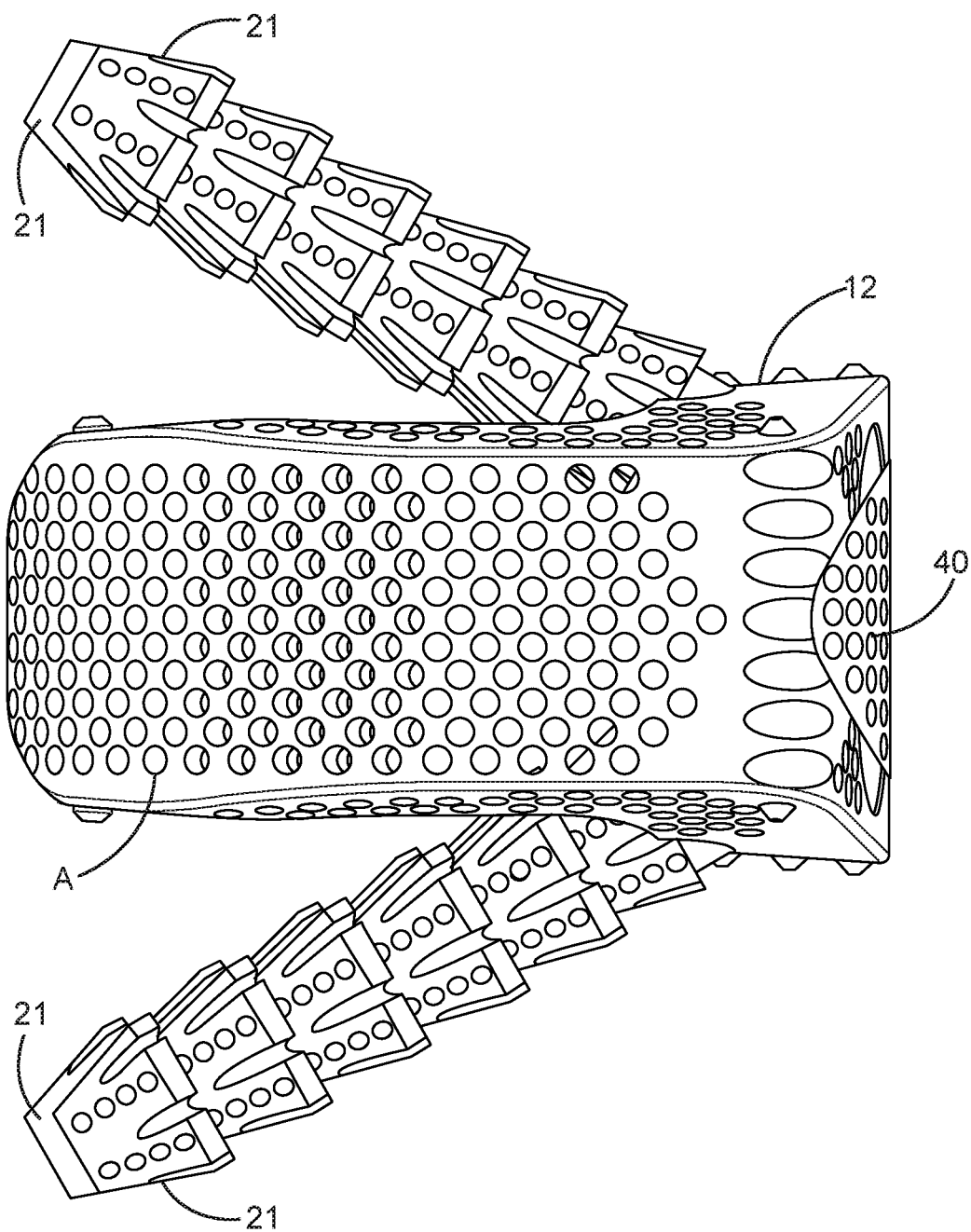
FIG. 3 is a side view of the interbody spinal fusion cage implant of FIG. 2.

Anchors 21 are inserted through two upper holes 20 and two lower holes 30 on cage 10, 11 and 12 so that each of cages 10, 11 and 12 has four anchors, which can anchor the cage to a set of vertebrae in the spinal column of a patient. Anchors 21 that are inserted through anchor holes 20 are anchored to a first vertebra (superior), and anchors 21 that are inserted through anchor holes 30 are anchored or secured to a second vertebra (inferior) that is inferior to the first vertebra. FIG. 3 is a side view that shows the orientation and angularity of the anchors relative to a cage, in this case cage 12, although the same is true with cages 10 and 11.

Figure 4:
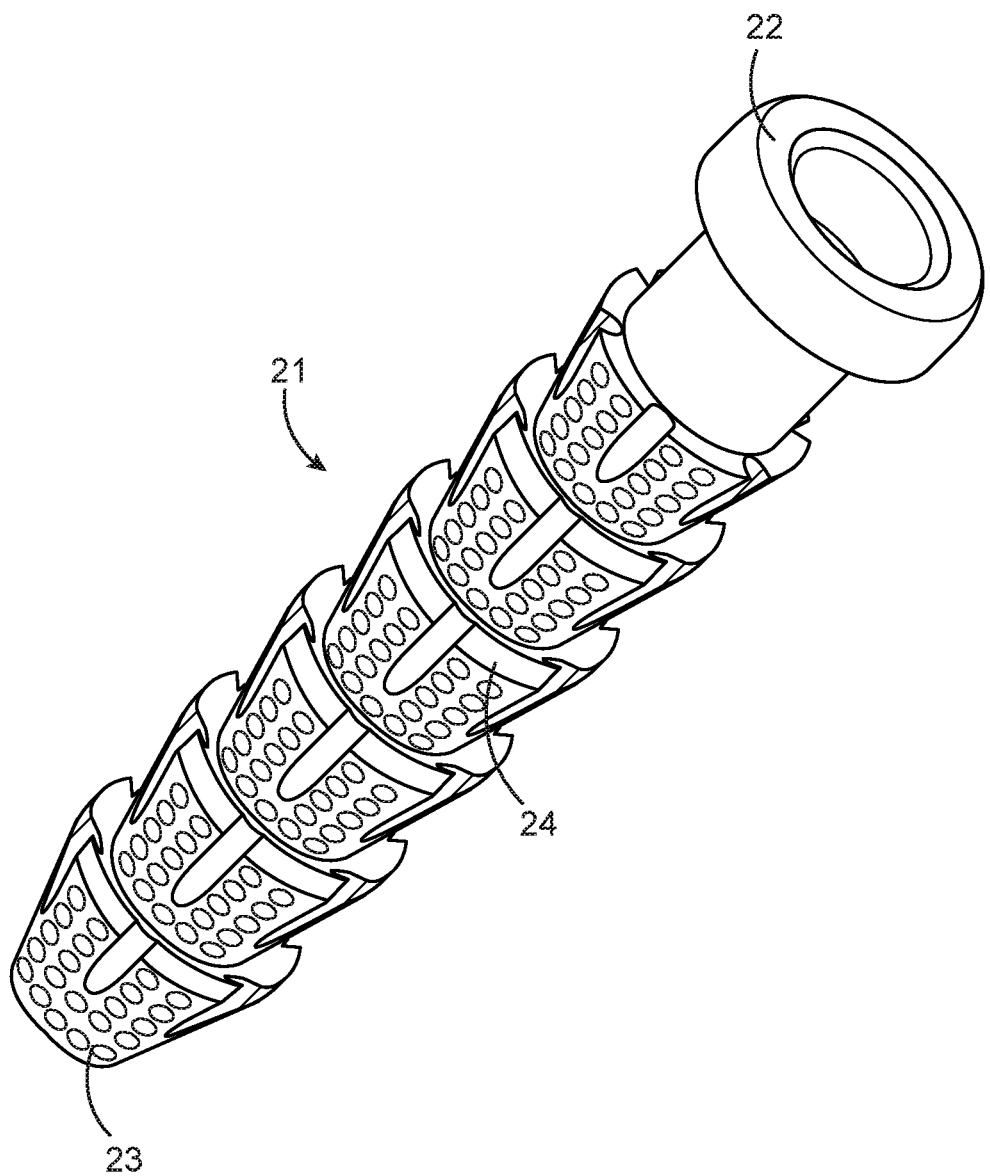
FIG. 4 is a perspective view of an anchor used in the interbody spinal fusion cage implant of FIG. 2.

FIG. 4 shows an anchor of the present invention. When anchoring cages to vertebra, typically screws are used in the prior art. In the present invention, however, anchors 21 are used instead of screws. Anchors 21 have multiple ridges 24 that drive into bone and secure anchors 21 to the vertebral bone so that the anchors won't dislodge from the bone. The head of the anchor 22 can be struck to advance the distal end 23 of anchor into bone and lodge anchor 21 into bone. In alternative embodiments, screws instead of anchors 21 can also be used, although they may not be as effective in long-term stability within the bone.

Figure 5:
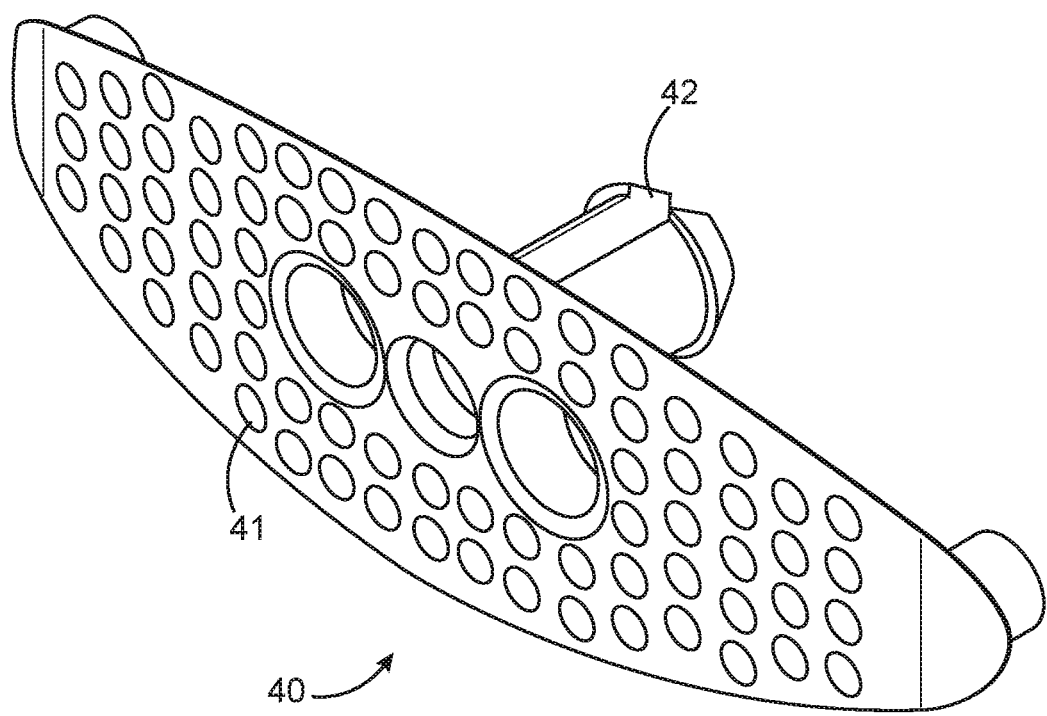
FIG. 5 is a perspective view of an anchor plate used to secure the anchors of the interbody spinal fusion cage implant of FIG. 2.
Figure 6:
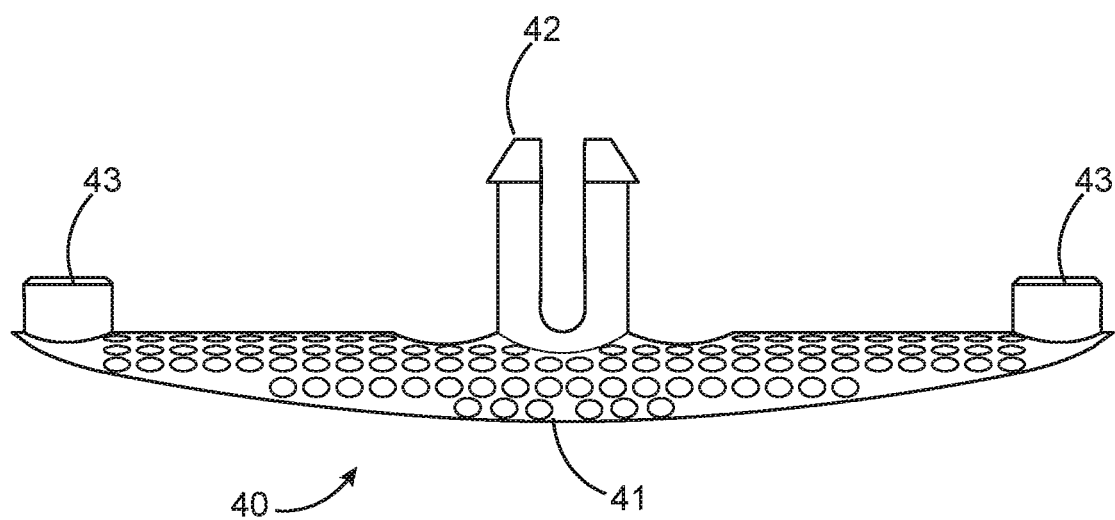
FIG. 6 is a top side view of the anchor plate of FIG. 5.

Anchor plate 40 is shown in FIG. 5. Anchor plate 40 has a bayonet lock 42 that locks the anchor plate 40 to any one of cages 10, 11 or 12 when the bayonet lock 40 mates with an opening in the center of the faces of cages 10, 11, and 12. This prevents any anchors 21 from falling out or disassociating from cages 10, 11 or 12. Front face 41 of anchor plate 40 can be tapped to engage and secure it to a cage 10, 11 or 12. Guide posts 43 are used to engage with guide holes in the faces of cages 10, 11 or 12. Like anchors 21, anchor plate 40 can be matched to the density of cages 10, 11 or 12.

In one embodiment, each kit 1 contains the following items: (i) a sealed green colored package containing cage 10, four anchors 21 that are matched in density with cage 10, and an anchor plate 40 that is matched in density with cage 10; (ii) a sealed yellow colored package containing cage 11, four anchors 21 (optional) that are matched in density with cage 11, and an anchor plate 40 (optional) that is matched in density with cage 11; (iii) a sealed red colored package containing cage 12, four anchors 21 (optional) that are matched in density with cage 12, and an anchor plate 40 (optional) that is matched in density with cage 12; (iv) an inserter 13 that is used to insert one of the cages into a disk space between two adjacent vertebrae; (v) instructions for use; and (vi) bone graft material (optional).

The instructions for use of kit 1 can include the following steps for use of the items found within kit 1:
  i. determine the DEXA scan T-score of the patient's native bone at the site of surgical intervention in the spine (this can be done prior to the surgical procedure and be included in the patient's medical records or chart and confirmed by the surgical physician just prior to or during the surgical procedure;

ii. choose a cage from among the three cages 10, 11 or 12 that most closely matches the native bone's BMD based on the DEXA scan T-score of the patient's native bone at the site of implantation by doing the following:
   1. If the patient's native bone has a DEXA Scan T-score of −1 or higher, i.e., in the normal range of BMD indicated by a T-score that is in the green range, retrieve the green package containing cage 10.
   2. If the patient's native bone has as DEXA Scan T-score of between −1 and −2.5, i.e., in the low range of BMD indicated by a T-score that is in the yellow range, retrieve the yellow package containing cage 11.
   3. If the patient's native bone has a DEXA Scan T-score lower than −2.5, i.e., in the very low range of BMD indicated by a T-score that is in the red range, retrieve the red package containing cage 12.
iii. Unseal the package that most closely matches your patient's DEXA scan T-score as indicated above, and do NOT unseal the other two sealed packages.
iv. Pack the bone graft material into the central hole B of the cage (optional) that you retrieved.
v. Take the cage from the unsealed package, which now has bone graft material in it (optional) and releasably couple it to the inserter.
vi. Use the inserter to guide the cage into the disk space at the site of intervention in the surgical procedure.
vii. Secure the cage within the spinal column using the four anchors that are in the same sealed package (now unsealed) as the cage that you used with this patient (optional).
viii. Secure the anchor plate over the exposed face of the cage by inserting the bayonet lock of the anchor plate into the opening on the face of the cage until it locks in place (optional).
ix. Once the procedure is completed, discard kit 1.

Other embodiments of kits are also contemplated herein. For example, a kit that doesn't contain anchors and the cages are self anchoring as a result of being serrated or having other mechanisms that don't require anchors.

The same principals discussed above with respect to interbody spinal fusion cages can be applied to other types of orthopedic implants, such as knee implants and hip implants. In one embodiment, a hip implant kit is described, which contains at least three femoral stems, each having outer dimensions that are virtually identical. However, they are not the same weight, density, porosity, or surface area. The first one is the most dense, heaviest, least porous, and has the least surface area; the second is middle in density, porosity, weight and surface area; and the third is the least dense, lightest in weight, most porous, and has the most surface area. The stems can be manufactured from implantable metal, plastic, reinforced plastic, titanium, titanium cobalt, stainless steel, cobalt-chromium alloys, titanium and cobalt mixed metal, ceramic, PEEK or carbon fiber, or any combination thereof. In one embodiment, they are manufactured from titanium.

In one embodiment, each of the hip implant stems has identifying indicia that indicates whether it is the most dense, middle density, or least dense of the 3 stems. For example, the stems can be numbered 1, 2 and 3 or the reverse etched into the stems. In another embodiment, their density may be identified by a +− and = signs etched into the stems. In another embodiment, the stems may have a color painted on an area of the stem or the entirety of the stem. For example, the first stem that is the most dense may be green; the second stem in middle density may be yellow; and the third stem with the least density may be red to match the typical DEXA Scan color coded results. In another embodiment, each of the stems is located within a sealed package of its own that itself has an identifier that indicates whether it is the most dense, middle density or least dense of the stems. For example, the first stem of the highest density may be in a sealed package that is green or has green markings on it; the second stem in middle density may be in a sealed package that is yellow or has yellow markings on it; and the third stem of lowest density may be in a sealed package that is red or has red markings on it. The purpose of this is so that the team of surgeons and staff that are involved in a surgical procedure can easily identify which of the stems they should use based on the DEXA scan T-score of the patient's hip, and they won't make a mistake by implanting the wrong stem.

In yet another embodiment, a kit contains 3 or more acetabular components each having outer dimensions that are virtually identical. However, they are not the same weight, and they do not have the same density, porosity, or surface area. The first one is the most dense, heaviest, least porous, and has the least surface area; the second is middle in density, porosity, weight and surface area; and the third is the least dense, lightest in weight, most porous, and has the most surface area. The acetabular components can be manufactured from implantable metal, plastic, reinforced plastic, titanium, titanium cobalt, stainless steel, cobalt-chromium alloys, titanium and cobalt mixed metal, ceramic, PEEK or carbon fiber or any combination thereof. In one embodiment, they are manufactured from titanium.

In one embodiment, each of the acetabular components has identifying indicia that indicate whether it is the most dense, middle density, or least dense of the components. For example, the components can be numbered 1, 2 and 3 or the reverse etched into the components. In another embodiment, their density may be identified by a +− and = signs etched into the components. In another embodiment, the components may have a color painted on an area of the component or the entirety of the component. For example, the first acetabular component that is the most dense may be green; the second acetabular component in middle density may be yellow; and the third acetabular component with the least density may be red to match the typical DEXA Scan color coded results. In another embodiment, each of the acetabular components is located within a sealed package of its own that itself has an identifier that indicates whether it is the most dense, middle density or least dense of the components. For example, the first component of the highest density may be in a sealed package that is green or has green markings on it; the second component in middle density may be in a sealed package that is yellow or has yellow markings on it; and the third component of lowest density may be in a sealed package that is red or has red markings on it.

In one embodiment, kit 1 is associated with a specific demographic. For example, it may be associated with white females, black females, white males, black males, Hispanic females, Hispanic males, Asian females, Asian males, or other demographics based on gender, race, ethnic origin, height, weight, physical condition, medications the patient takes, history of illness or current illness, or other factor for which there may be a reference database for DEXA Scan T-scores. The specific kit that most closely matches a patient can be used, because the cages in that kit can have densities that are matched with the DEXA Scan T-score reference database that most closely matches that patient in terms of gender, race, ethnic origin, country of nationality or other factor.

Each of the kits described above can contain a instructions for use during a surgical procedure on a patient. The instructions can contain the following steps, which are described with respect to a kit containing 3 or more implants of the same type but different density/weight/surface area/porosity:

i. determine the DEXA scan T-score of the patient's native bone at a site of surgical intervention in the spine (this can be done prior to the surgical procedure and be included in the patient's medical records or chart and confirmed by the surgical physician just prior to or during the surgical procedure in which an orthopedic implant is introduced into the patient;

ii. choose the implant from among the three implants that most closely matches the native bone's BMD based on the DEXA scan T-score;
   1. If the patient has a DEXA Scan T-score of −1 or higher, i.e., in the normal range of BMD indicated by a T-score that is in the green range, choose the implant that has a green indicia (or other indicia indicating highest density among the three cages) or is in green packaging;
   2. If the patient has as DEXA Scan T-score of between −1 and −2.5, i.e., in the low range of BMD indicated by a T-score that is in the yellow range, choose the implant which has a yellow indicia (or other indicia indicating medium density among the 3 cages) or is in yellow packaging;
   3. If the patient has a DEXA Scan T-score lower than −2.5, i.e., in the very low range of BMD indicated by a T-score that is in the red range, choose the implant, which has a red indicia (or other indicia indicating least density among the three cages) or is in the red packaging.

iii. Introduce the implant to the patient's native bone at the site of surgical intervention to the exclusion of the other two implants.

iv. Once the procedure is completed, discard the kit.

In another embodiment, a method of treating a patient who requires surgical implantation of an orthopedic implant is described. The method includes the steps of: determining the DEXA scan T-score of the patient's native bone at a site of surgical implantation where the implant will be in contact with the patient's native bone; choosing from among three or more otherwise identical implants an implant that has a density that is closest to the density of the patient's native bone at the site of surgical implantation based on the DEXA scan T-score of the patient's native bone; and using said implant in the surgical procedure to the exclusion of the other two or more implants.

In one embodiment, the method of treatment involves implanting an interbody spinal fusion cage in the spinal column. The physician or medical team performing the surgery may determine the patient's gender, race and/or ethnic origin or this step may be skipped. The physician may determine other factors unique to the patient as well, such as height, weight, physical condition, the medications the patient takes, history of illness or current illness. The physician or medical team performing the surgery then determines the DEXA scan T-score of the native bone at either or both the vertebra above and the vertebra below the location where the cage will be implanted. Once the DEXA scan T-score is determined, the physician or medical team performing the surgery will choose an interbody spinal fusion cage from among 3 or more cages that most closely matches the patient's DEXA scan T-score for either or both of the vertebrae that were scanned relative to the other two implants. The DEXA scan T-score may use a general reference such as a healthy person have peek bone at 30 years of age, or it may use a more specific reference, such as a black male. If a more specific reference is used, then a kit that is matched to that reference will be used rather than a kit that is matched to a general reference. If the DEXA scan T-score is in the green range or a score of −1 or higher indicating healthy bone in the normal range, then the cage having an indicia of highest density/weight and lowest surface area/porosity is chosen from among the 3 or more cages. That indicia may be a number, a sign, or a color on the cage or on the packaging of the cage. For example, the cage may be in a sealed package that is green or has green markings to indicate that it is the cage with the highest density/lowest porosity/greatest weight/lowest surface area. If the DEXA scan T-score is in the yellow range or a score of between about −1 and about −2.5 indicating bone that is lower than normal in density, then the cage having an indicia of medium density/porosity/surface area/weight is chosen from among the 3 or more cages. Again, that indicia may be a number, a sign or a color on the cage or on the packaging of the cage. For example, the cage may be in a sealed package that is yellow or has yellow markings to indicate that it is the cage with the medium amount of density/porosity/surface area/weight from among the three or more cages. If the DEXA scan T-score is in the red range or a score of −2.5 or lower indicating very low bone density and osteoporosis, then the cage having an indicia of low density/weight and high porosity/surface area is chosen from among the 3 or more cages. Again, this indicia may be a number, sign or color on the cage or on the packaging of the cage. For example, the cage may be in a sealed package that is red or has red markings to indicate that it is the cage with the lowest density/weight and highest porosity/surface area from among the three or more cages. Once the physician or medical team has chosen the interbody cage based on the DEXA scan T-score of the particular patient, that interbody cage is implanted in the spinal column at the site of intervention to the exclusion of the other two cages. This process may be repeated for any further cages that are to be implanted in the patient at other sites along the spinal column by matching the correct cage with the site of intervention based on the DEXA scan T-score for the additional site(s) of intervention along the spinal column.

While the is susceptible to various modifications and alternative forms, specific examples thereof have been shown by way of example in the drawings and are herein described in detail. It should be understood, however, that the invention is not to be limited to the particular forms or methods disclosed, but to the contrary, the invention is to cover all modifications, equivalents, and alternatives falling within the spirit and scope of the appended claims.

We claim:

1. A kit for orthopedic surgical procedures comprising:
   three or more similar orthopedic implants, wherein a first of said implants has a first density, the second implant has a second density that is lower than the first density, and the third implant has a third density that is lower than the first and second densities;
   instructions for use during a surgical procedure on a patient comprising the following steps:
      determine the DEXA scan T-score of the patient's native bone at a site of surgical intervention;
      if the DEXA scan T-score of the patient's native bone is −1 or higher, then retrieve the first implant and introduce it to the patient's native bone to the exclusion of the second and third implants;

if the DEXA scan T-score of the patient's native bone is between a −2.5 and −1.0, then retrieve the second implant and introduce it to the patient's native bone to the exclusion of the first and third implants;

if the DEXA scan T-score of the patient's native bone is lower than −2.5, then retrieve the third implant and introduce it to the patient's native bone to the exclusion of the first and second implants.

2. The kit of claim 1, wherein the three or more implants each has a unique indicia that identifies its density relative to the others of the three implants.

3. The kit of claim 2, wherein the indicia of the first implant is that it is green in color or has a green marking on it.

4. The kit of claim 2, wherein the indicia of the second implant is that it is yellow in color or has a yellow marking on it.

5. The kit of claim 2, wherein the indicia of the third implant is that it is red in color or has a red marking on it.

6. The kit of claim 1, wherein the three or more implants is each within its own sealed package within the kit and each package is a different color.

7. The kit of claim 6, wherein the package of the first implant is green or has green markings, the package of the second implant is yellow or has yellow markings, and the package of the third implant is red or has red markings.

8. The kit of claim 1, wherein the implants are interbody cages for spine fusion, femoral stems of a hip implant, or acetabular components of a hip implant.

9. The kit of claim 8, wherein the three or more implants have the same outer dimensions as one another, but the first implant weighs more than the second implant and the second implant weighs more than the third implant.

10. The kit of claim 9, wherein the third implant has more surface area than the second implant, and the second implant has more surface area than the first implant.

11. The kit of claim 9, wherein the third implant has greater porosity than the second implant, and the second implant has greater porosity than the first implant.

12. The kit of claim 8, wherein the implants are interbody cages for spine fusion.

13. The kit of claim 12, wherein the first implant has a density of about 4.40 g/cm$^3$, 3.90 g/cm$^3$, 3.00 g/cm$^3$ or 1.40 g/cm$^3$.

14. The kit of claim 12, wherein the second implant has a density of about 3.80 g/cm$^3$, 3.30 g/cm$^3$, 2.00 g/cm$^3$ or 1.00 g/cm$^3$.

15. The kit of claim 12, wherein the third implant has a density of about 3.20 g/cm$^3$, 2.50 g/cm$^3$ 1.50 g/cm$^3$ or 0.80 g/cm$^3$.

16. The kit of claim 12, wherein the first implant has a density that falls within the range of about 1.10 g/cm$^3$ to about 1.80 g/cm$^3$, the second implant has a density that falls within the range of about 0.90 g/cm$^3$ to about 1.10 g/cm$^3$, and the third implant has a density that falls within the range of about 0.60 g/cm$^3$ to about 0.90 g/cm$^3$.

17. The kit of claim 8, wherein the implants are femoral stems of a hip implant.

18. The kit of claim 8, wherein the implants are acetabular components of a hip implant.

19. A method of treating a patient who requires surgical implantation of an orthopedic implant, said method comprising the steps of:

determining a DEXA scan T-score of the patient's native bone at a site of surgical implantation where the implant will be in contact with the patient's native bone;

retrieve from among three or more similar implants an implant that has a density that is closest to the density of the patient's native bone at the site of surgical implantation based on the DEXA scan T-score of the patient's native bone; and implanting the retrieved implant in the patient to the exclusion of the other two or more implants.

20. The method of claim 19, wherein the implant is an interbody cage for spine fusion.

21. The method of claim 19, wherein the implant is a femoral stem of a hip implant or an acetabular component of a hip implant.

22. The method of claim 19, wherein if the DEXA scan T-score of the patient's native bone is −1.0 or higher, then a first implant is retrieved, wherein the first implant has the highest density among the three or more implants; if the DEXA scan T-score of the patient's native bone is between −1.0 and −2.5, then a second implant is chosen, wherein the second implant has a lower density than the first implant but a higher density than a third implant; and if the DEXA scan T-score of the patient's native bone is lower than −2.50, then the third implant is chosen, wherein the third implant has a lower density than either the first implant or the second implant.

23. The method of claim 22, wherein the first implant is retrieved from a sealed package that is green; the second implant is retrieved from a sealed package that is yellow; and the third implant is retrieved from a sealed package that is red.

* * * * *